United States Patent [19]

Himmele et al.

[11] Patent Number: 4,824,862
[45] Date of Patent: Apr. 25, 1989

[54] 3-PHENYL-2-STYRYLPYRROLIDINES, PREPARATION AND USE THEREOF

[75] Inventors: Walter Himmele, Walldorf; Gerd Steiner, Kirchheim; Hans-Juergen Teschendorf, Dudenhofen; Harald Weifenbach, Ludwigshafen, all of Fed. Rep. of Germany

[73] Assignee: BASF Aktiengesellschaft, Ludwigshafen, Fed. Rep. of Germany

[21] Appl. No.: 197,275

[22] Filed: May 23, 1988

[30] Foreign Application Priority Data

May 23, 1987 [DE] Fed. Rep. of Germany ....... 3717394

[51] Int. Cl.$^4$ ................. C07D 207/06; C07D 207/08; A61K 31/40
[52] U.S. Cl. ..................................... 514/429; 548/577
[58] Field of Search ......................... 548/577; 514/429

[56] References Cited

U.S. PATENT DOCUMENTS 3,669,973  6/1972  Borck et al. .................... 548/577
4,273,787  6/1981  Galantay ...................... 514/429 X

OTHER PUBLICATIONS

"Rote Liste 1985" by Bundesverband der Pharmazeutischen Industrie (1985) (pages not given).

Primary Examiner—Joseph Paul Brust
Attorney, Agent, or Firm—Oblon, Fisher, Spivak, McClelland & Maier

[57] ABSTRACT

Novel 3-phenyl-2-styrylpyrrolidines of the formula I

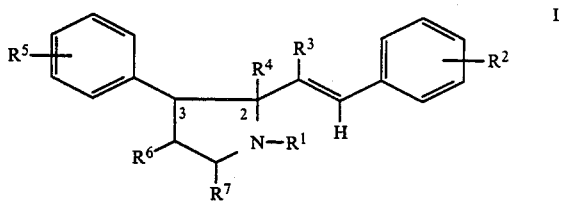

where $R^1$–$R^7$ have defined meanings, are suitable for treating disorders.

12 Claims, No Drawings

3-PHENYL-2-STYRYLPYRROLIDINES, PREPARATION AND USE THEREOF

The present invention provides novel 3-phenyl-2-styrylpyrrolidines, a process for preparing same and a method of using same for treating disorders.

The prior art discloses a number of active substances which are used as sedatives and tranquilizers for treating psychic disorders (cf. Rote Liste 1985, Indication groups 48 B1 and 70 B4).

We have now found that a novel class of compounds, namely 3-phenyl-2-styrylpyrrolidines of the formula I

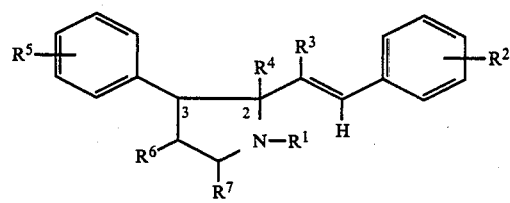
I where $R^1$ is hydrogen or $C_1$-$C_6$-alkyl, $R^2$ and $R^5$ are each hydrogen, halogen, $C_1$-$C_3$-alkyl, $C_1$-$C_3$-alkoxy, $C_1$-$C_3$-alkylthio or trifluoromethyl, and $R^3$, $R^4$, $R^6$ and $R^7$ are each hydrogen or $C_1$-$C_3$-alkyl, and salts thereof with physiologically tolerated acids, are highly suitable for treating psychic disorders.

Of the compounds of the formula I, preference is given to those where $R^1$ is hydrogen, methyl, ethyl or n-propyl, $R^2$ and $R^5$ are each hydrogen, fluorine, chlorine or trifluoromethyl and $R^3$, $R^4$, $R^6$ and $R^7$ are each hydrogen.

The novel compounds can be present as cis and/or trans isomers and also as racemates or optical antipodes:

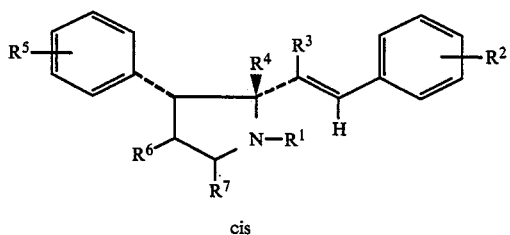

cis

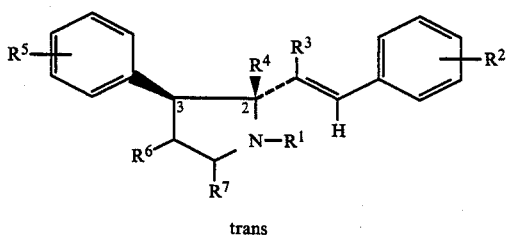

trans

Specific examples are in particular the following compounds: cis-3-phenyl-2-trans-styryl-N-methylpyrrolidine, trans-3-phenyl-2-trans-styryl-N-methylpyrrolidine, cis-3-phenyl-2-trans-styryl-N-ethylpyrrolidine, trans-3-phenyl-2-trans-styryl-N-ethylpyrrolidine, cis-3-phenyl-2-trans-styryl-N-n-propylpyrrolidine and trans-3-phenyl-2-trans-styryl-N-n-propylpyrrolidine.

The novel compounds are preparable by
(a) hydrogenating a compound of the formula II

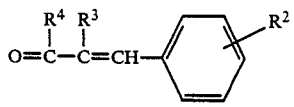
II where $R^2$–$R^4$ are as defined above, and a compound of the formula III

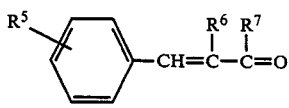
III where $R^5$–$R^7$ are as defined above, together with an amine of the formula IV $$R^1NH_2 \qquad\qquad IV$$

where $R^1$ is as defined above, in the presence of a catalyst based on a metal of the iron group at 70°–150° C. or
(b) if $R^3$, $R^4$ and $R^6$ are each hydrogen, reducing a compound of the formula V

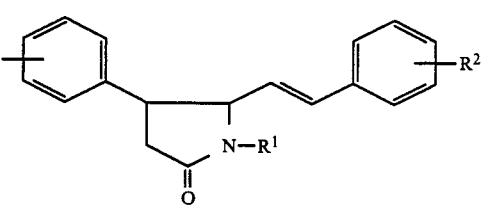
V where $R^1$, $R^2$ and $R^5$ are as defined above, and if desired converting the compounds thus obtained into their salts with physiologically tolerated acids.

In process (a), 1 mole of compound II and 1 mole of compound III react with 1 mole of amine IV with the uptake of 2 moles of hydrogen.

The reaction is carried out at from 70° to 150° C., preferably at from 80° to 110° C., in particular at from 85° to 100° C. The hydrogenation takes place under a hydrogen pressure of from 30 to 250 bar, the best yields being obtained in the range 120 to 180 bar.

A suitable catalyst for the hydrogenation is a metal of the iron group, in particular cobalt or nickel. Particularly high utility is possessed by cobalt of the Raney type which has been partially deactivated by storage or heat treatment or by a mild treatment with air. The catalyst used in the Examples for the reaction of the α,β-unsaturated carbonyl compounds was a Raney cobalt whose reactivity had been reduced by storage for 200–600 hours in water at from 70° to 90° C. Also suitable for the reaction is a Raney nickel whose hydrogenation activity has been reduced. If the deactivation of the catalyst is overdone, the hydrogenation gives primarily high-boiling condensation products. An overactive catalyst gives in particular the regular reaction products of aminating hydrogenation.

The reaction is carried out in a solvent such as ethanol or tetrahydrofuran in an autoclave. The compounds of the formula I are most simply purified by fractional distillation.

Reduction (b) is carried out with the aid of a complex metal hydride, preferably lithium aluminum hydride, in an inert organic solvent, preferably tetrahydrofuran, at from 0° to 80° C.

The starting compounds of the formula V are also preparable from 1-alkyl-4-phenyl-5-formylpyrrolidin-2-one derivatives (German Laid-Open Applications DOS No. 3,537,075 and DOS No. 3,632,589) by Wittig reaction with benzylphosphonium salts or benzylphosphates in the presence of bases.

Any mixtures obtained of diastereoisomers of the formula I can be separated into the pure diastereoisomers in cis or trans configuration, preferably by fractional crystallization from a lower alcohol. The pure diastereoisomers can be resolved, if desired, into the corresponding antipodes in a conventional manner, for example by forming diastereoisomers salts with the aid of optically active acids. For example, the free base of the formula I is dissolved in a lower alcohol and 1 equivalent of (±)- or (−)-tartaric acid, (+)- or (−)-dibenzoyltartaric acid or (+)- or (−)-di-p-toluoyltartaric acid is added. The fractional crystallization then first gives the less soluble of the two diastereoisomeric salts, which is crysstallized until a constant angle of rotation is obtained. Freeing the free base then gives the enantiomerically pure form of compound I.

The number of isomers formed in the reaction according to the invention can be reduced by selecting identical substances for starting materials II and III. This option is a preferred method of working the invention.

The free 3-phenyl-2-styrylpyrrolidines of the formula I can be converted into the acid addition salt of a pharmacologically tolerated acid in a conventional manner, preferably by admixing a solution with an equivalent of the corresponding acid. Pharmaceutically tolerated acids are for example hydrochloric acid, phosphoric acid, sulfuric acid, methanesulfonic acid, sulfamic acid, maleic acid, fumaric acid, oxalic acid, tartaric acid and citric acid.

The novel substances are suitable for treating psychic disorders, in particular depressions.

The mode of action of a group of therapeutically frequently used antidepressants (for example tricyclic antidepressants) include the inhibition of the neuronal uptake of transmitter substances (norepinephrine, dopamine, serotonin). This property is utilized in biological test models to characterize potential antidepressants.

The following method was used: Inhibition of neurotransmitter uptake in rat brain synaptosomes Hippocampus, corpus striatum and cortex of rat brains were dissected out and homogenized in 0.32M sucrose solution. Differential centrifugation gave synaptosomes which were suspended in buffer solution. Synaptosomes are capable of actively taking up added neurotransmitter substances (for example norepinephrine, dopamine, serotonin) from the surrounding medium. With the aid of uptake inhibitors it is possible to counteract this process to a degree which depends on the concentration. The synaptosomes were mixed with the test substances in various concentrations and then incubated at 37° C. with $^3$H-norepinephrine (hippocampus), $^3$H-dopamine (corpus striatum) and $^3$H-serotonin (cortex). The substrate concentration was about 10 mM. The uptake was determined by dilution with ice-cold buffer solution; thereafter the synaptosomes were separated off by centrifugation, and the $^3$H activity was measured in the sediment. A blank value was determined by incubating at 0° C.

The median inhibitory concentration (IC 50) was calculated from the inhibitor values found for the various inhibitor concentrations by comparison with the blank test by linear regression following logit-log conversion.

| Substance of Example No. | Inhibition of neurotransmitter uptake in synaptosomes | | |
| --- | --- | --- | --- |
| | Norepinephrine IC 50 $\mu$M/l | Dopamine IC 50 $\mu$M/l | Serotonin IC 50 $\mu$M/l |
| 1 cis | 0.029 | 0.12 | >1.0 |
| 1 trans | 0.0073 | 0.092 | >1.0 |
| 2 cis | 0.043 | 0.18 | >1.0 |
| 2 trans | 0.0055 | 0.023 | >1.0 |
| 3 cis | −0.4 | −1.0 | >1.0 |
| trans | 0.16 | 0.4 | >1.0 |
| Imipramine | 0.014 | >1.0 | 0.13 |

The compounds according to the invention are remarkable in that they inhibit not only the uptake of noradrenaline but also the uptake of dopamine while the uptake of serotonin is not affected. The substaces thus differ in profile from imipramine, a prototype of a clinically proven antidepressant. As to potency, the inhibition of noradrenaline uptake by imipramine is in some instances appreciably exceeded by the compounds according to the invention (Example 1 trans, Example 2 trans). The inhibition of dopamine uptake is an additional activity component not possessed by imipramine.

The present invention accordingly also provides a therapeutic composition which contains a compound of the formula I or a pharmacologically tolerated acid addition salt thereof, as an active substance, as well as customary carriers and diluents, and also a method of using the novel compounds in the treatment of disorders.

The compounds according to the invention can be administered in a conventional manner orally or parenterally, intravenously or intramuscularly.

The dose depends on the age, state and weight of the patient and on the route of administration. In general, the daily dose of active substance ranges from about 1 to 20 mg/kg of weight in the case of oral administration and from 0.1 to 2 mg/kg of weight in the case of parenteral administration.

The novel compounds can be employed in the conventional solid or liquid pharmaceutical forms, such as tablets, film-coated tablets, sugar-coated tablets, capsules, powders, granules, suppositories, solutions, salves, creams or sprays. These are prepared in a conventional manner, and to do so the active substances can be mixed with conventional pharmaceutical auxiliaries such as tablet binders, fillers, preservatives, disintegrants, glidants, emollients, wetting agents, dispersants, emulsifiers, solvents, retardants, antioxidants and/or propellant gases (cf. H. Sucker et al.: Pharmazeutische Technologie, Thieme-Verlag, Stuttgart, 1978). The application forms thus obtained normally contain the active substance in an amount of from 1 to 99% by weight.

EXAMPLE 1 cis- and trans-3-Phenyl-2-trans-styryl-N-methylpyrrolidine

A 10 l stirred autoclave was charged with 1.4 kg of monomethylamine, 1.6 kg of ethanol and 0.1 kg of Raney cobalt. The autoclave was heated to 100° C. and charged with hydrogen under a pressure of 150 bar. 1.6 kg of cinnamaldehyde was pumped in over 10 hours. After the uptake of hydrogen had ceased, the reaction mixture was cooled down, filtered and subjected to fractional distillation. The fraction which came over at 153°–184° C./2 mbar contained 99.5 g of cis-3-phenyl-2-trans-styryl-N-methylpyrrolidine and 68.5 g of trans-3-phenyl-2-trans-styryl-N-methylpyrrolidine.

The mixture of diastereoisomers thus obtained was separated by fractional distillation through a packed column containing a stainless steel wire mesh helix (length 160 cm). The cis diastereoisomer passed over at 157° C./2 mbar and was more than 95% pure (melting point of hydrochloride: 190°–191° C.), while the trans diastereoisomer passed over at 160°–161° C./2 mbar and was more than 90% pure (melting point of hydrochloride: 202°–204° C.).

EXAMPLE 2 cis- and trans-3-Phenyl-2-trans-styryl-N-ethylpyrrolidine

In a 10 l autoclave, 2.0 kg of cinnamaldehyde were reacted with 1.4 kg of ethylamine at 90° C. under a hydrogen pressure of 150 bar in the presence of 100 g of Raney cobalt in 1.6 kg of ethanol. The cinnamaldehyde was pumped in over 10 hours. After addition of cinnamaldehyde the reaction conditions were maintained for a further 6 hours.

The reaction mixture was subsequently subjected to fractional distillation. A fraction obtained at 160°–165° C./2 mbar contained 141 g of cis- and 161 g of trans-3-phenyl-2-trans-styryl-N-ethylpyrrolidine. The diastereoisomers were separated as in Example 1. Melting points: cis-hydrobromide 220°–223° C., trans-hydrochloride 144°–146° C.

EXAMPLE 3 cis- and trans-3-Phenyl-2-trans-styryl-N-n-propylpyrrolidine

In a 10 l autoclave, 2 kg of cinnamaldehyde were reacted with 1.6 kg of n-propylamine at 90° C. under a hydrogen pressure of 150 bar in the presence of 100 g of Raney cobalt. The cinnamaldehyde was pumped in over 10 hours. The reaction mixture was subjected to fractional distillation. The fraction passing over at 150°–200° C./2 mbar was subjected to fractional distillation as described in Example 1 giving at 164°–166° C./2 mbar cis-3-phenyl-2-trans-styryl-N-n-propylpyrrolidine (85% pure) and at 167°–168° C./2 mbar trans-3-phenyl-2-trans-styryl-N-n-propylpyrrolidine (94% pure).

The same method was used to prepare the following substituted cis- and trans-3-phenyl-2-trans-styrylpyrrolidine derivatives by using correspondingly substituted cinnamaldehyde or benzalacetone derivatives in the aminating hydrogenation:

4. cis- and trans-2,5-dimethyl-3-phenyl-2-trans-styryl-N-methylpyrrolidine
5. cis- and trans-2,5-dimethyl-3-phenyl-2-trans-styryl-N-ethylpyrrolidine
6. cis- and trans-4-methyl-3-phenyl-2-trans-β-methylstyryl-N-ethylpyrrolidine.

EXAMPLE 7 cis-1-Methyl-3-phenyl-2-trans-m-chlorostyrylpyrrolidine (a) Preparation of starting material 32.8 g (77 mmol) of n-butyllithium (15% in hexane) were added dropwise under nitrogen with ice cooling to 36.0 g (77 mmol) of triphenyl-m-chlorobenzylphosphonium bromide in 150 ml of toluene in the course of 20 minutes, and the orange suspension was subsequently stirred for 15 minutes. 15.6 g (77 mmol) of cis-5-formyl-1-methyl-4-phenylpyrrolidin-2-one (German Laid-Open Applications DOS No. 3,537,075 and DOS No. 3,632,589; J. Org. Chem. 52 (1987), 4352) in 120 ml of toluene were then added dropwise and stirred in at room temperature for 3 hours (color change toward pale yellow). 200 ml of $H_2O$ were then added, the mixture was acidified with dilute HCl and filtered with suction, the phases were separated, the aqueous phase was extracted twice more with toluene, and the combined organic phases were washed with $H_2O$, dried and concentrated. The crude product was taken up in 100 ml of methyl t-butyl ether and filtered with suction and cooling to remove precipitated triphenylphosphine oxide. The filtrate was concentrated and purified by column chromatography (silica gel, eluent: 98/2 methylene chloride/methanol); yield: 16.1 g (67%). Judging by a $^1H$-NMR spectrum, the styryl side chain is 90% in the trans configuration and 10% in the cis configuration.

(b) Preparation of end product

A solution of 3.0 g (9.6 mmol) of cis-1-methyl-4-phenyl-5-m-chlorostyrylpyrrolidin-2-one in 40 ml of ether was added dropwise at from 0° to 5° C. under nitrogen to 0.65 g (17 mmol) of lithium aluminum hydride in 30 ml of ether, and the mixture was subsequently stirred for 1 hour with ice cooling. 10% strength sodium hydroxide solution was then slowly added dropwise with cooling until the precipitate formed a conglomerate on the walls of the vessel. The supernatant ether phase was washed with $H_2O$ (pH 10), dried and concentrated. Purification by column chromatography (silica gel, eluent: 95/5 methylene chloride/methanol) gave cis-1-methyl-3-phenyl-2-trans-m-chlorostylpyrrolidine as the free base (2.3 g, 80%). This base was taken up in ethyl acetate and converted with ethereal HCl into the hydrochloride; melting point: 53°–56° C.

The same method, by using trans-5-formyl-1-methyl-4-phenylpyrrolidin-2-one, gives the trans diastereoisomer.

8. cis- and trans-3-Phenyl-2-trans-o-chlorostyryl-N-methylpyrrolidine.
9. cis- and trans-3-Phenyl-2-trans-m-chlorostyryl-N-methylpyrrolidine.
10. cis- and trans-3-Phenyl-2-trans-p-chlorostyryl-N-methylpyrrolidine.
11. cis- and trans-3-Phenyl-2-trans-m-fluorostyryl-N-methylpyrrolidine.
12. cis- and trans-3-Phenyl-2-trans-p-fluorostyryl-N-methylpyrrolidine.
13. cis- and trans-3-Phenyl-2-trans-m-methylstyryl-N-methylpyrrolidine.
14. cis- and trans-3-Phenyl-2-trans-p-methylstyryl-N-methylpyrrolidine.
15. cis- and trans-3-Phenyl-2-trans-2,4-dichlorostyryl-N-methylpyrrolidine.
16. cis- and trans-3-Phenyl-2-trans-m-methoxystyryl-N-methylpyrrolidine.
17. cis- and trans-3-Phenyl-2-trans-p-trifluoromethylstyryl-N-methylpyrrolidine.
18. cis- and trans-3-Phenyl-2-trans-o-fluorostyryl-N-methylpyrrolidine.
19. cis- and trans-3-Phenyl-2-trans-p-thiomethylstyryl-N-methylpyrrolidine.

20. cis- and trans-3-Phenyl-2-trans-p-methoxystyryl-N-methylpyrrolidine.

EXAMPLE 21

A tablet press was used to press tablets in a conventional manner from the following composition:
12.5 mg of substance of Example 1 (cis)
120 mg of corn starch
13.5 mg of gelatin
45 mg of lactose
2.25 mg of Aerosil ® (chemically pure silica in submicroscopically fine division)
6.75 mg of potato starch (as 6% strength paste)

EXAMPLE 22

Sugar-coated tablets are prepared in a conventional manner from the following composition:
7.5 mg of substance of Example 1 (trans)
60 mg of core material
60 mg of sugar-coating material The core material comprises 9 parts of corn starch, 3 parts of lactose and 1 part of Luviskol$^R$ VA 64 (vinylpyrrolidine/vinyl acetate copolymer, 60:40; cf. Pharm. Ind. 1962, 586). The sugar-coating material comprises 5 parts of cane sugar, 2 parts of corn starch, 2 parts of calcium carbonate and 1 part of talc. The sugar-coated tablets thus prepared are then coated with an overcoat resistant to gastric juices.

EXAMPLE 23

1 g of substance of Example 2 (cis) in the form of the hydrochloride is dissolved in 5000 ml of water in the presence of NaCl, and the solution is brought to pH 6.0 with 0.1N NaOH to give a blood isotonic solution. 5 ml each of this solution are introduced into ampoules and sterilized.

We claim:
1. A 3-phenyl-2-styrylpyrrolidine of the formula I

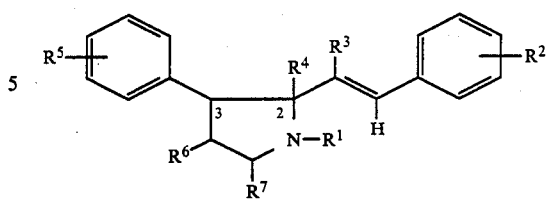

where $R^1$ is hydrogen or $C_1$–$C_6$-alkyl; $R^2$ and $R^5$ are each independently one substituent on each phenyl ring selected from the group consisting of halogen, $C_1$–$C_3$-alkyl, $C_1$–$C_3$-alkoxy, $C_1$–$C_3$-alkylthio or trifluoromethyl, or one or both of $R^2$ and $R^5$ may be hydrogen, the remaining positions on the phenyl rings being hydrogen atoms; and $R^3$, $R^4$, $R^6$ and $R^7$ are each hydrogen or $C_1$–$C_3$-alkyl, or a salt thereof with a physiologically tolerated acid.

2. A compound of the formula I as claimed in claim 1 where $R^1$ is hydrogen, methyl, ethyl or n-propyl, $R^2$ and $R^5$ are each hydrogen, fluorine, chlorine or trifluoromethyl and $R^3$, $R^4$, $R^6$ and $R^7$ are each hydrogen.

3. A compound as claimed in claim 2 where $R^2$ and/or $R^5$ are each hydrogen.

4. cis-3-Phenyl-2-trans-styryl-N-methylpyrrolidine.
5. trans-3-Phenyl-2-trans-styryl-N-methylpyrrolidine.
6. cis-3-Phenyl-2-trans-styryl-N-ethylpyrrolidine.
7. trans-3-Phenyl-2-trans-styryl-N-ethylpyrrolidine.
8. cis-3-Phenyl-2-trans-styryl-N-n-propylpyrrolidine.
9. trans-3-Phenyl-2-trans-styryl-N-n-propylpyrrolidine.

10. A therapeutic composition comprising a pharmaceutically acceptable carrier and an antidepressant effective amount of a compound of claim 1 as the active substance.

11. The method of treating depressions in a patient suffering therefrom which comprises administering an antidepressant effective amount of a compound of claim 1.

12. A compound according to claim 1, wherein said physiologically tolerated acid is selected from the group consisting of hydrochloric acid, phosphoric acid, sulfuric acid, methanesulfonic acid, sulfamic acid, maleic acid, fumaric acid, oxalic acid, tartaric acid and citric acid.

* * * * *